(12) United States Patent
Blasche et al.

(10) Patent No.: US 7,906,769 B2
(45) Date of Patent: Mar. 15, 2011

(54) PARTICLE ACCELERATOR FOR RADIOTHERAPY BY MEANS OF ION BEAMS

(75) Inventors: Klaus Blasche, Darmstadt (DE); Bernhard Franczak, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 488 days.

(21) Appl. No.: 11/629,805

(22) PCT Filed: Jun. 16, 2005

(86) PCT No.: PCT/EP2005/006491
§ 371 (c)(1),
(2), (4) Date: Jul. 7, 2008

(87) PCT Pub. No.: WO2005/125289
PCT Pub. Date: Dec. 29, 2005

(65) Prior Publication Data
US 2008/0290297 A1 Nov. 27, 2008

(30) Foreign Application Priority Data

Jun. 16, 2004 (DE) .................. 20 2004 009 421 U

(51) Int. Cl.
*H01J 1/50* (2006.01)
(52) U.S. Cl. ............ 250/492.3; 250/396 ML; 250/491.1
(58) Field of Classification Search .................. 250/298, 250/492.3, 396, 492.21, 492.1, 491.1, 396 ML
See application file for complete search history.

(56) References Cited

U.S. PATENT DOCUMENTS
4,992,746 A  2/1991 Martin
5,200,701 A * 4/1993 Siebold et al. ................ 324/309
(Continued)

FOREIGN PATENT DOCUMENTS
EP        0 994 638       4/2000
WO    WO-00/16342 A1    3/2000
(Continued)

OTHER PUBLICATIONS

Hattori et al., Nuclear Instruments and Methods in Physics Research B, 188:221-224 (2002).

(Continued)

*Primary Examiner* — Jack I Berman
*Assistant Examiner* — Meenakshi S Sahu
(74) *Attorney, Agent, or Firm* — Peter F. Corless; Christine C. O'Day; Edwards Angell Palmer & Dodge LLP

(57) ABSTRACT

The invention relates to a particle accelerator for radiotherapy by means of ion beams (150). The particle accelerator comprises a sixfold synchrotron ring (100) having six rectilinear beam sections (1 to 6) and six curved beam sections (7 to 12). Injection means (43) for introducing a linearly accelerated ion beam into the synchrotron ring (100) are arranged on a first rectilinear beam section (1) of the six rectilinear beam sections (1-6). Along the course of a second rectilinear beam section (5) there is at least one acceleration means (44) for the ion beam. Extraction means (45) for extracting the internal beam highly accelerated after several circulations are provided on a third rectilinear beam section (4). Each curved beam section (7 to 12) comprises a pair of dipole magnets (13/14, 15/16, 17/18, 19/20, 21/22, 23/24). A horizontally defocusing quadrupole magnet (31 to 36) is arranged between each pair of dipole magnets (13/14, 15/16, 17/18, 19/20, 21/22, 23/24), and a horizontally focusing quadrupole magnet (25 to 30) is arranged upstream of each pair of dipole magnets (13/14, 15/16, 17/18, 19/20, 21/22, 23/24).

14 Claims, 13 Drawing Sheets

U.S. PATENT DOCUMENTS

| | | |
|---|---|---|
| 5,285,166 A | 2/1994 | Hiramoto et al. |
| 6,008,499 A * | 12/1999 | Hiramoto et al. .......... 250/492.3 |
| 6,087,670 A | 7/2000 | Hiramoto et al. |
| 2002/0014588 A1 * | 2/2002 | Hiramoto et al. ............. 250/298 |

OTHER PUBLICATIONS

Office Action corresponding to Chinese Patent Application No. 2005800195352.

* cited by examiner

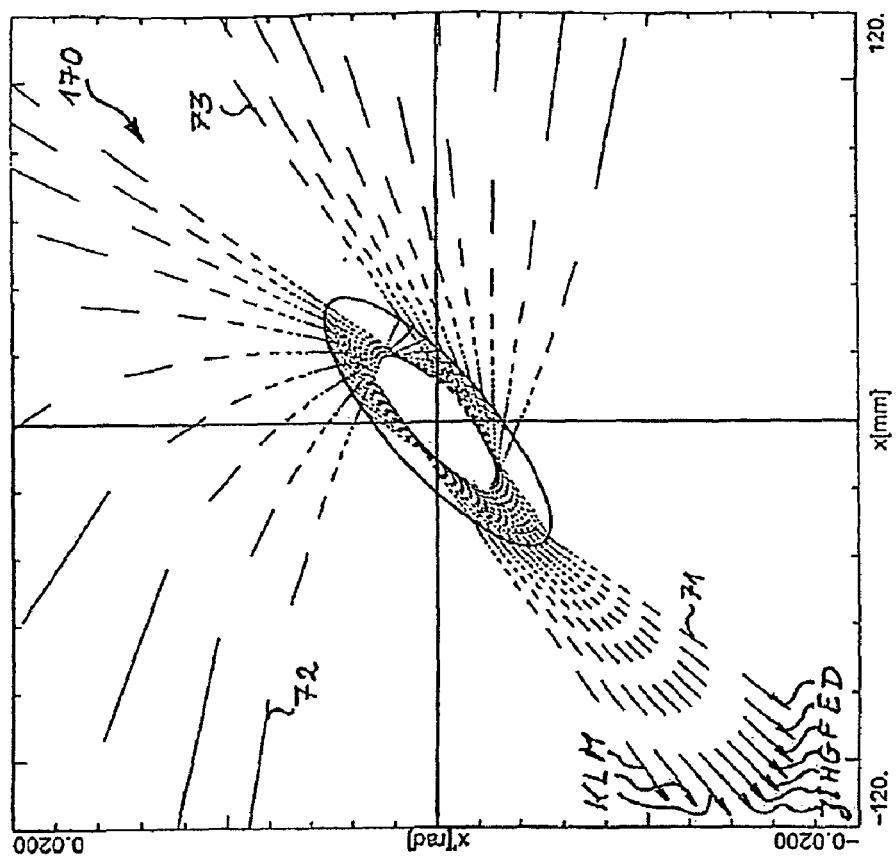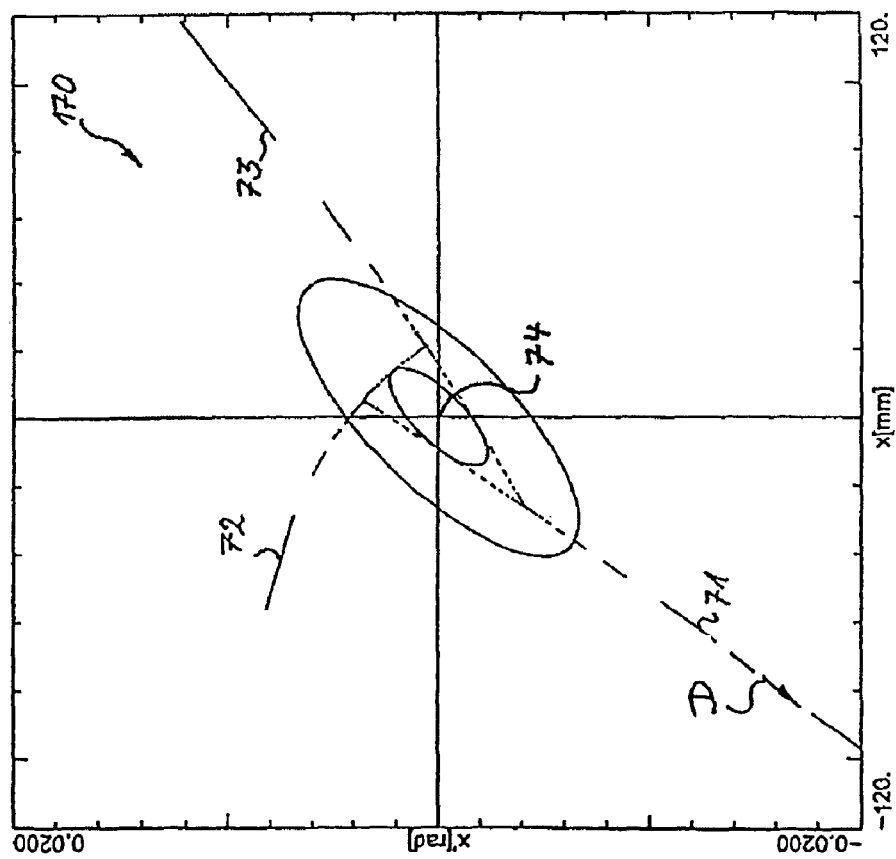

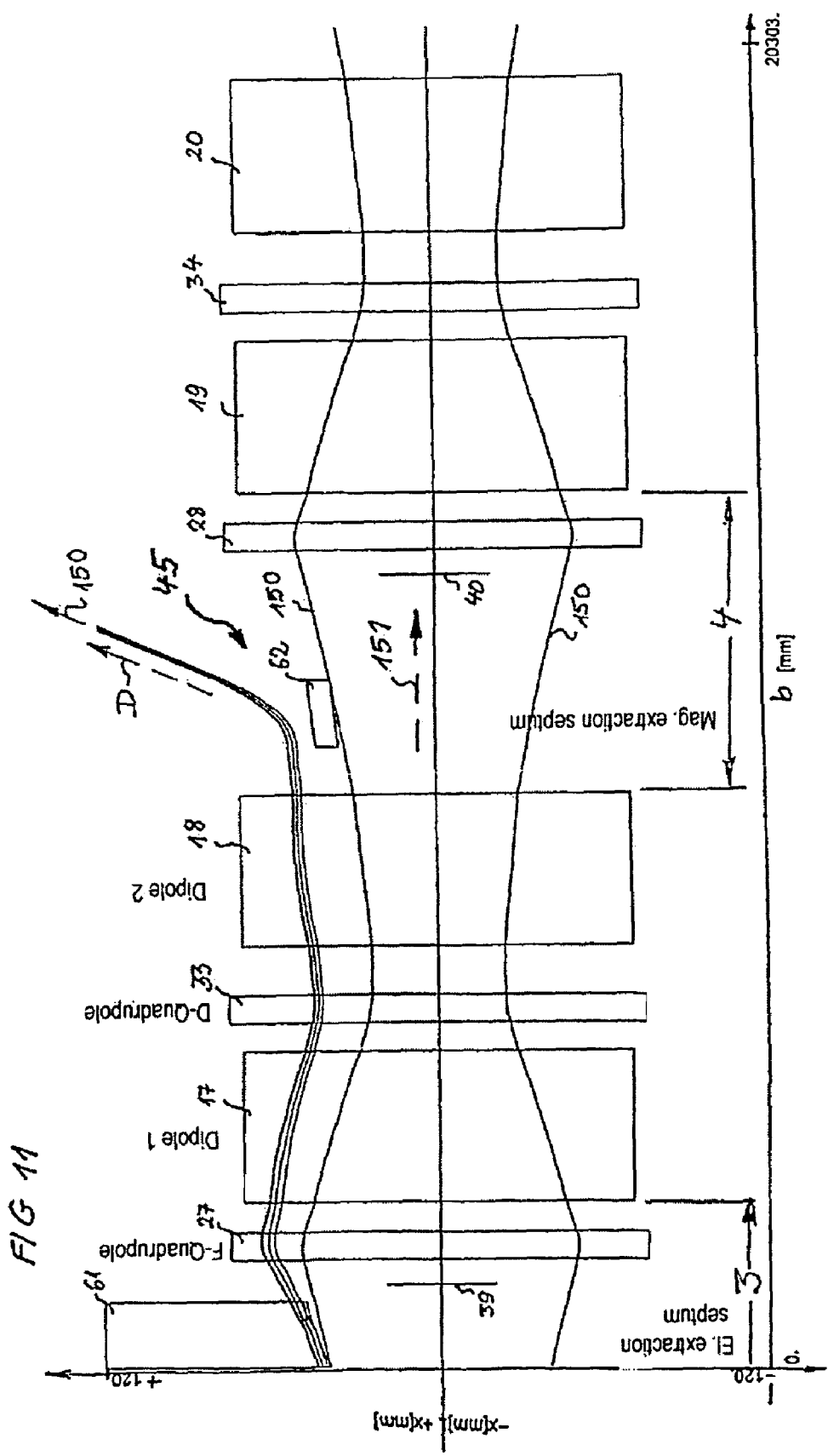

PARTICLE ACCELERATOR FOR RADIOTHERAPY BY MEANS OF ION BEAMS

The invention relates to a particle accelerator for radiotherapy by means of ion beams. Such a particle accelerator is known from the publication DE 100 10 523 C2 and as components of the particle accelerator comprises different ion sources that ionise different materials, a mass spectrometer for selecting the ions, an accelerator for linear preaccleration of the ions, and injection means for introducing the ions into a sixfold synchrotron ring. The sixfold synchrotron ring is used for further high acceleration of the ions. Furthermore, the known particle accelerator comprises extraction means for decoupling the highly accelerated ions from the synchrotron ring into a beam guidance section with deflecting magnets to corresponding irradiation sites in patients.

The main item in the high acceleration of an ion beam in a particle accelerator for radiotherapy by mean of ion beams is the synchrotron ring, in which, by means of a plurality of controlled circulations in the synchrotron ring in accordance with an acceleration cycle, the ions are supplied with exactly enough energy to destroy a volume element of diseased tissue at a predetermined depth, without damaging the healthy covering tissue above it. Accordingly, in a synchrotron, as opposed to a cyclotron, from cycle to cycle different radiation doses are generated, each with only as much radiation energy as is required to reach different pre-set depths. In a cyclotron, a maximum predetermined radiation energy is generated consistently from cycle to cycle without regard to the required need, which increases the radiation burden on the environment, since the radiation energy required at any one time is adjusted after the acceleration by deceleration in absorbers of suitable thickness. In this process, only a small part of the accelerated particle beam can be used for therapeutic irradiation, which contravenes environmental protection guidelines.

The sixfold synchrotron ring known from the above publication having six rectilinear beam sections and six curved beam sections comprises on a first rectilinear beam section injection means for introducing a linearly accelerated ion beam into the synchrotron ring, and in the course of a second rectilinear beam section possesses at least one acceleration means for the ion beam, and at a third rectilinear beam section, after several circulations, at the end of a cycle decouples, using extraction means, the dosage-adjusted highly accelerated ion beam into the beam guidance section. Over and above that, in the known synchrotron ring three bumper magnets are arranged on the straight beam sections which, after injection of the ions into the synchrotron ring, in a plurality of circulations centre the ion beam, one of the bumper magnets being arranged in the rectilinear beam section in which also injection means are arranged.

For that purpose, in the known sixfold synchrotron ring, in each of the curved beam sections there is arranged an elongate, solid, tonne-weighing dipole magnet having an H-type configuration of coil and pole piece, for horizontal deflection of the ion beam through 60° and, for horizontal stabilisation of the ion beam, a horizontally focusing quadrupole magnet and a horizontally defocusing quadrupole magnet are arranged in succession upstream of the entry of the ion beam into the aperture of the dipole magnet.

One disadvantage of the known particle accelerator with synchrotron ring is the long distance that the ion beam has to cover through the dipole magnets until the next rectilinear beam section is reached. This requires an aperture that opens wide. This is unfavourably associated with the use of a dipole magnet that is complex in terms of materials with a large requirement of electrical pulse power, which increases the investment costs for the magnet and magnet power supply as well as the operating costs. Added to this are stringent technical requirements of the foundations on which the elongate, solid and tonne-weighing dipole magnets are to be fixedly arranged, which puts a strain on building and investment costs. Finally, there also problems involved in maintenance and repair, since heavy lifting and transporting equipment commensurate with the masses to be moved is needed, which increase the running costs. Furthermore, the large dimensions of the dipole magnets necessitate disadvantageous use of at least two septum magnets as extraction means, which in a rectilinear beam section are capable of guiding the beam during extraction past the dipole magnets and out of the synchrotron ring.

The concept of the active raster-scan method with the energy of the ion beam adjustable from pulse to pulse has proved successful for radiotherapy by means of ion beams. The best accelerator type for this form of irradiation technology is the synchrotron. At the GSI Darmstadt the heavy ion synchrotron SIS has been used successfully for many years for the development of radiotherapy by means of ion beams. At the University Hospital in Heidelberg a new accelerator system with a small synchrotron is currently being built for the clinical application of radiotherapy by means of ion beams, as is known from the publication: The Proposed Dedicated Ion Beam Facility for Cancer Therapy at the Clinic in Heidelberg, EPAC 2000.

The heavy ion synchrotron SIS is a far larger accelerator system, which is designed according to different technical concepts. The accelerator system in Heidelberg, however, is equipped with the above-described sixfold synchrotron, which is associated with the stated disadvantages pertaining to the size and weight of the dipole magnets and related components, such as quadrupoles, bumper magnets and septum magnets for example, and pertaining to investment, building and operating costs.

The invention is based on the technical problem of producing a particle accelerator for radiotherapy by means of ion beams that overcomes the drawbacks in the art and provides a particle accelerator for radiotherapy by means of ion beams that under full electronic control reliably provides a precision ion beam for radiotherapy by means of ion beams.

That problem is solved with the subject matter of the independent claim 1. Advantageous developments of the invention are apparent from the dependent claims.

Thus, according to the invention, a particle accelerator for radiotherapy by means of ion beams is provided, wherein the particle accelerator comprises a synchrotron ring (100) having rectilinear beam sections (1 to 6), curved beam sections (7 to 12), injection means (43), extraction means (45) and at least one acceleration means (44), wherein at least one curved beam section (7 to 12) comprises a pair of dipole magnets (13/14, 15/16, 17/18, 19/20, 21/22, 23/24), a horizontally defocusing quadrupole magnet (31 to 36) is arranged between the pair of dipole magnets (13/14, 15/16, 17/18, 19/20, 21/22, 23/24), and a horizontally focusing quadrupole magnet (25 to 30) is provided upstream of the pair of dipole magnets (13/14, 15/16, 17/18, 19/20, 21/22, 23/24).

Further, in accordance with the invention a particle accelerator for radiotherapy by means of ion beams is provided, wherein the particle accelerator comprises a synchrotron ring having rectilinear beam sections and curved beam sections. Injection means for introducing a linearly accelerated ion beam into the synchrotron ring are arranged on one rectilinear beam section of the rectilinear beam sections. Along the course of another rectilinear beam section there is at least one acceleration means for the ion beam. Extraction means for extracting the ion beam highly accelerated after several circulations are provided on a further rectilinear beam section. At least one of the curved beam sections comprises a pair of dipole magnets, a horizontally defocusing quadrupole magnet being arranged between the pair of dipole magnets, and a focusing quadrupole magnet being arranged upstream of the pair of dipole magnets.

The advantage of this particle accelerator is that the long, curved beam section, which was previously formed by an elongate, solid and tonne-weighing dipole magnet having an H-type configuration of coil and pole piece, is shared between a pair of dipole magnets comprising two dipole magnets. Because of the shorter path length of the ion beam within a respective dipole of the dipole pair, it is advantageously possible to reduce the aperture appreciably and correspondingly to make the dipoles lighter in weight and give them an improved coil and pole piece configuration. In addition, the arrangement of the dipole pair according to the invention provides an advantageous opportunity to position the horizontally defocusing quadrupole magnet between the dipole pair, which further minimises the requirements regarding the aperture and quadrupole strength. The dipoles of a dipole magnet pair are preferably arranged closely one behind the other in the curved beam section so that exactly one defocusing quadrupole can be arranged between the dipole magnets of the dipole magnet pair.

The dipole magnet pair preferably has a coil configuration comprising a combination of a window-frame magnet type and an H-magnet type, which can also be called a WF/H-type. This advantageous magnet type is possible owing to the shortened trajectory length and reduced aperture, and allows the use of dipole magnets having a considerably smaller cross-section and correspondingly lower weight as well as a much-reduced requirement for electrical pulse power.

Furthermore, in a preferred embodiment of the invention, the bumper magnets are arranged outside the rectilinear beam section for the injection means in the three other of the six rectilinear beam sections, in such a way that one bumper magnet is arranged downstream of the injection means and at least one bumper magnet is arranged upstream of the injection means. This embodiment has the advantage that the rectilinear beam section for the injection means is not overloaded, so that consistently six short rectilinear beam sections are possible, which has a favourable effect on the overall size of the synchrotron ring.

Furthermore, it is intended to allow the ion beam after injection of the ions to be centred by means of just two bumper magnets, and hence to reduce the investment costs further.

For an injection of the ion beam within a limited number of circulations the bumper magnets preferably have mains adapters and control units, which for control of a reducing exciting current provide a non-linear ramp with a flattened-off course at the end of the ramp. In an advantageous manner the injection means for the synchrotron are thus more reliably configured for what is termed multi-turn injection, by providing a non-linear, e.g. parabolic, ramp for the magnetic fields of the bumper magnets with a steep drop at the start of the ramp and with a course that flattens out at the end of the ramp, and by reliably and precisely achieving the trajectory displacement with at most three bumper magnets in place of the known arrangement with four bumper magnets, no bumper magnet being required in the very tightly packed injection section.

Moreover, in a further preferred embodiment an optimum geometry is achieved for the electrostatic injection septum, with beam entry in the centre of the aperture and beam exit at the internal electrode of the septum and with precise beam setting by adjustment of the two parameters deflection voltage at the electrostatic injection septum and automatic adjustment for the angle of incidence of the injected ion beam at the entry into the injection septum, owing to the fact that the injection means comprise an electrostatic injection septum, the curved electrostatic deflectors of which have a larger radius of curvature than the trajectory radius of the pre-accelerated, injected and deflected ion beam.

In a further preferred embodiment of the invention, the extraction means for exciting the non-linear resonance for precise adjustment of the separatrix and correspondingly the angle of emergence of the extracted beam comprise, as electronically exactly controllable extraction means, six individually adjustable, sextupole magnets upstream of each curved beam section and dipole magnet pair. In addition, the exciting currents of the individual sextupole magnets for the resonance extraction are adjustable, and the sextupole magnets are in operative connection with a fixed electrostatic extraction septum as one of the extraction means for extracting the ion beam. Further, an electrostatic extraction septum as well as just one septum magnet for the beam deflection in place of two septum magnets and also optimised technical design of the bending and quadrupole magnets in the synchrotron ensure great reliability in respect of the extraction angle.

The particle accelerator preferably comprises as one of the ion sources at least one laser ion source for the generation of beam pulses of carbon ions. With such an ion source it is possible to generate ion beams that comprise preferably carbon ions with the charge state q=4 ($C^{4+}$-ions). This laser ion source has the following advantages over other ion sources:
  (a) high beam intensities of more than $1 \cdot 10^{10}$ $C^{4+}$-ions in short beam pulses of 20-30 µs duration,
  (b) long lifetimes of several weeks without service,
  (c) high reliability over many years of operation, and
  (d) favourable investment and operating costs.

In a further preferred embodiment of the invention, the particle accelerator comprises a linear accelerator with IH section modules as injector linear accelerator, and quadrupole lens modules outside vacuum systems of the IH section modules. Such a linear accelerator has the following advantages over the known accelerating chamber for linear pre-acceleration:
  (a) modular construction of the linear accelerator with three short accelerator sections of 1.5-2 m long for what is termed the IH section,
  (b) modular construction of the high-frequency systems with HF generators of at most 180 kW HF output with corresponding simplification compared with systems in the hitherto customary performance category 1-2 MW to 2 MW,
  (c) technically simpler and for service more advantageous installation of the quadrupole lenses between the accelerator sections outside the vacuum system, e.g. through mechanical separation of the quadrupole yoke in a plane of symmetry,
  (d) high reliability over many years of operation, and
  (e) favourable investment and operating costs.

Furthermore, between the irradiation sites and the sixfold synchrotron there are provided beam guidance systems, which feature compensation of the horizontal dispersion directly after the synchrotron ring and for the distribution by vertical deflection onto the different irradiation sites. A high stability of the beam position at the irradiation sites is consequently advantageously achieved, wherein by means of the exclusively vertical deflection, a plurality of irradiation sites can be supplied with different angles of incidence α with $0 \leq \alpha \leq 90°$, 0° being a horizontal angle of incidence and 90° being an angle of incidence α impinging perpendicularly from above.

The invention will now be explained in greater detail with reference to the accompanying Figures.

FIG. 9 shows schematically a diagram with an exit direction of the extracted ion beam by means of the six individually adjustable sextupole magnets;

FIG. 10 shows schematically a diagram with a plurality of different exit directions of the extracted ion beam by means of the six individually adjustable sextupole magnets;

FIG. 11 shows schematically a diagram of the beam deflection in the synchrotron ring in the region of an extraction means;

Figure 1:
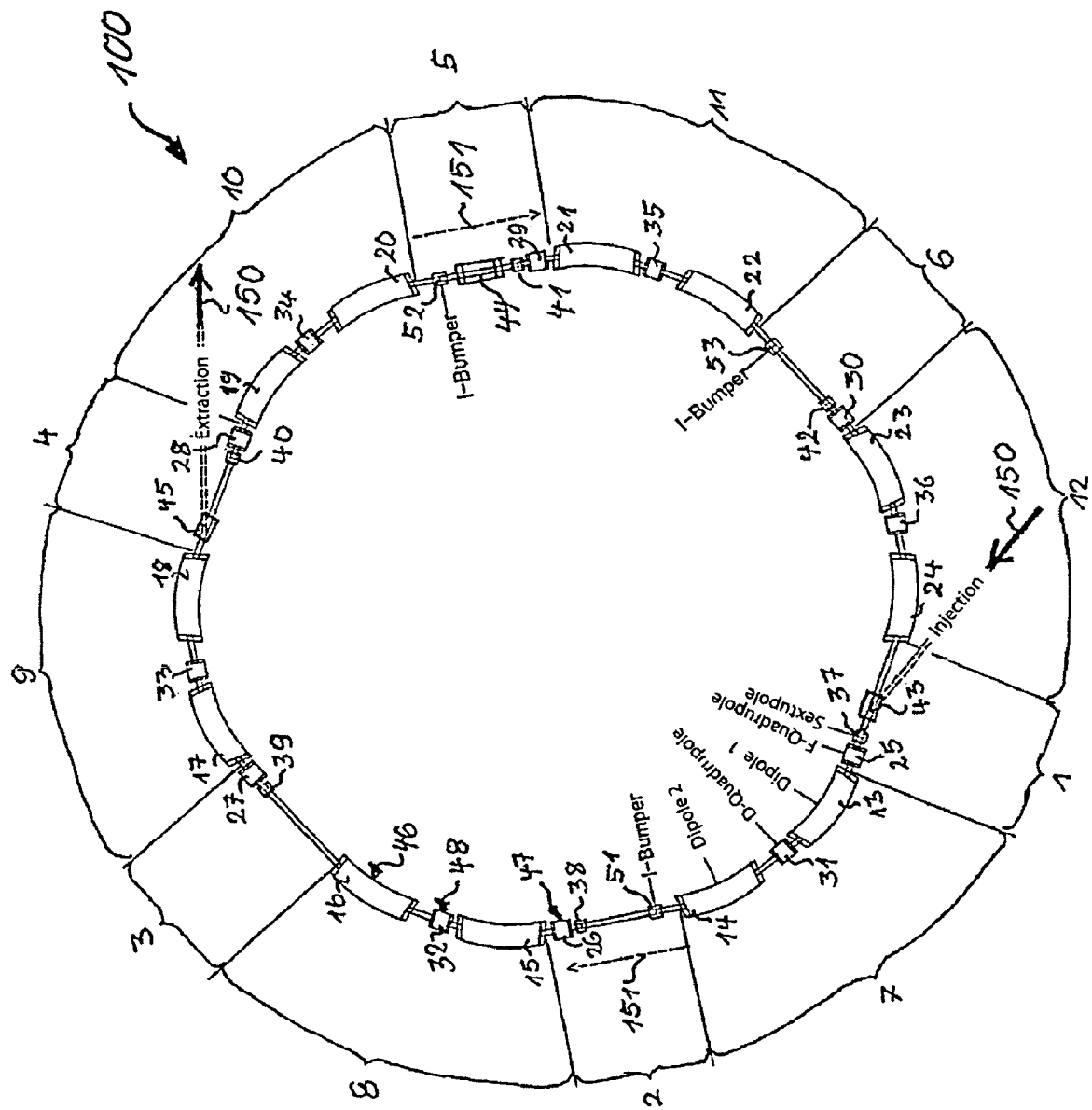
FIG. 1 shows schematically a plan view of a sixfold synchrotron ring of a particle accelerator in one embodiment of the invention.

FIG. 1 shows schematically a plan view of a sixfold synchrotron ring 100 of a particle accelerator in one embodiment of the invention. The sixfold synchrotron ring 100 has for this purpose six rectilinear beam sections 1 to 6 and six curved beam sections 7 to 12. Injection means 43 for introducing a linearly accelerated ion beam 150 into the synchrotron ring 100 are arranged on a first rectilinear beam section 1 of the six rectilinear beam sections 1 to 6. Along the course of a second rectilinear beam section 5 there is at least one acceleration means 44 for the ion beam 150. Extraction means 45 for extracting the ion beam, rapidly accelerated after several circulations, in the beam direction 151 are provided on a third rectilinear beam section 4.

In addition, each curved beam section 7 to 12 comprises a pair of dipole magnets 13/14, 15/16, 17/18, 19/20, 21/22 and 23/24. A horizontally defocusing quadrupole magnet 31 to 36 is arranged between the two dipole magnets of a pair of dipole magnets 13/14, 15/16, 17/18, 19/20, 21/22, 23/24 respectively. A horizontally focusing quadrupole magnet 25 to 30 is moreover arranged upstream of each pair of dipole magnets 13/14, 15/16, 17/18, 19/20, 21/22 and 23/24. The synchrotron thus has an optimum arrangement of dipole magnets 13 to 24 as bending magnets 46 and quadrupole magnets 25 to 36. In this arrangement, pairs of dipole magnets 13/14, 15/16, 17/18, 19/20, 21/22 and 23/24 as bending magnets and quadrupole magnets in a structure F (focusing magnet 47), BM (bending magnet 46), D (defocusing magnet 48) and BM (bending magnet 46) in six super-periods as curved beam sections 7 to 12 alternate with six free rectilinear beam sections 1 to 6.

An optimised magnet system with 12 light-weight dipole magnets 13 to 24, which are designed as a combination of window-frame and H-magnet, are thus used for the synchrotron. This magnet system has the following advantages over other designs:

(a) Reduction in the overall weight of all magnets, for example, to together less than 100 t compared with more than 210 t in the prior art with comparable side constraints of the system for injected and extracted ion beam energy, (b) maximum magnet weights of the individual magnets of at most 5 t and, for a bending magnet pair, of at most 10 t, and correspondingly simple mounting and demounting compared with more than 25 t for an individual bending magnet pair in the prior art with comparable side constraints of the system, accompanied by a clear reduction in weight and costs, (c) substantial reduction in the required pulse power for the magnet power supplies owing to the smaller aperture of the bending magnet pairs now possible compared with individual bending magnets, and correspondingly lower costs for the construction and operation of the particle accelerator.

These advantages are achieved by using modified magnet designs for the dipole magnets 13 to 24 and quadrupole magnets 25 to 36 as illustrated in the following Figures, and by selecting a different magnet arrangement with twelve dipole magnets 13 to 24 and twelve quadrupole magnet 25 to 36, as shown in FIG. 1.

Figure 2:
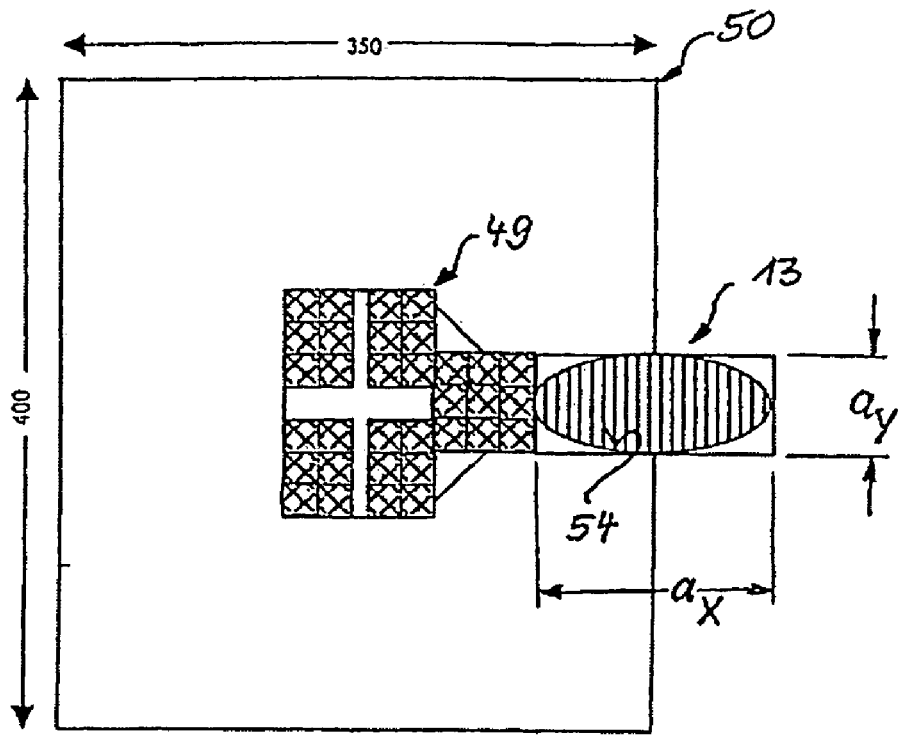
FIG. 2 shows schematically a partial cross-section through one dipole magnet of a pair of dipole magnets of the sixfold synchrotron ring according to FIG. 1.

FIG. 2 shows schematically a partial cross-section through one dipole magnet 13 of a pair of dipole magnets 13/14 i.e. bending magnet pair of the sixfold synchrotron ring 100 according to FIG. 1, just one laterally reversed half 50 of the dipole magnet 13 being shown. The dimensions are specified by way of example in millimetres. The elliptical aperture profile 54 enclosed by pole pieces and the magnet coil configuration 49 are characteristic of this combination of window-frame and H-magnet type, which can be created only on the basis of the inventive shortened curved beam sections per dipole magnet of the synchrotron ring. An optimum construction of the dipole magnet 13 with regard to the required magnet apertures $a_x$ in the horizontal direction and $a_y$ in the vertical direction in the synchrotron is achieved by the inventive optimised technical design of the bending and quadrupole magnets.

Figure 3:
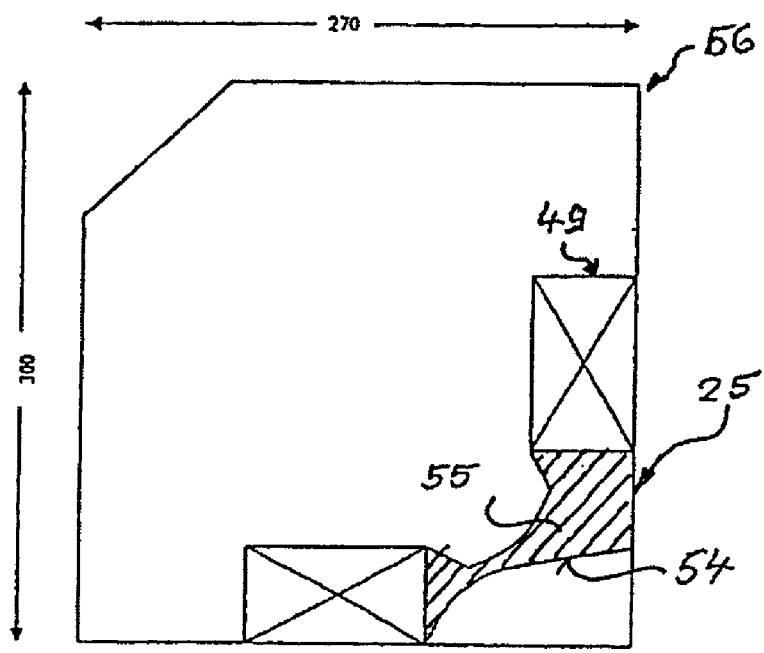
FIG. 3 shows schematically a partial cross-section through a quadrupole magnet of the sixfold synchrotron ring according to FIG. 1.

FIG. 3 shows schematically a partial cross-section through a quadrupole magnet 25 of the sixfold synchrotron ring 100 according to FIG. 1. Here, FIG. 3 shows merely a quadrant 56 of the quadrupole magnet in cross-section. The dimensions are specified by way of example in millimetres. This schematic cross-section illustrates the construction of the quadrupole magnet 25 with a rectangular profile and correspondingly small overall breadth. The magnetic coil configuration 49 and the pole piece configuration 55 differ from that of the dipole magnet 13 in FIG. 2 and are optimised with regard to weight and also with regard to the stored energy and the energy consumption during operation of the synchrotron.

Figure 4:
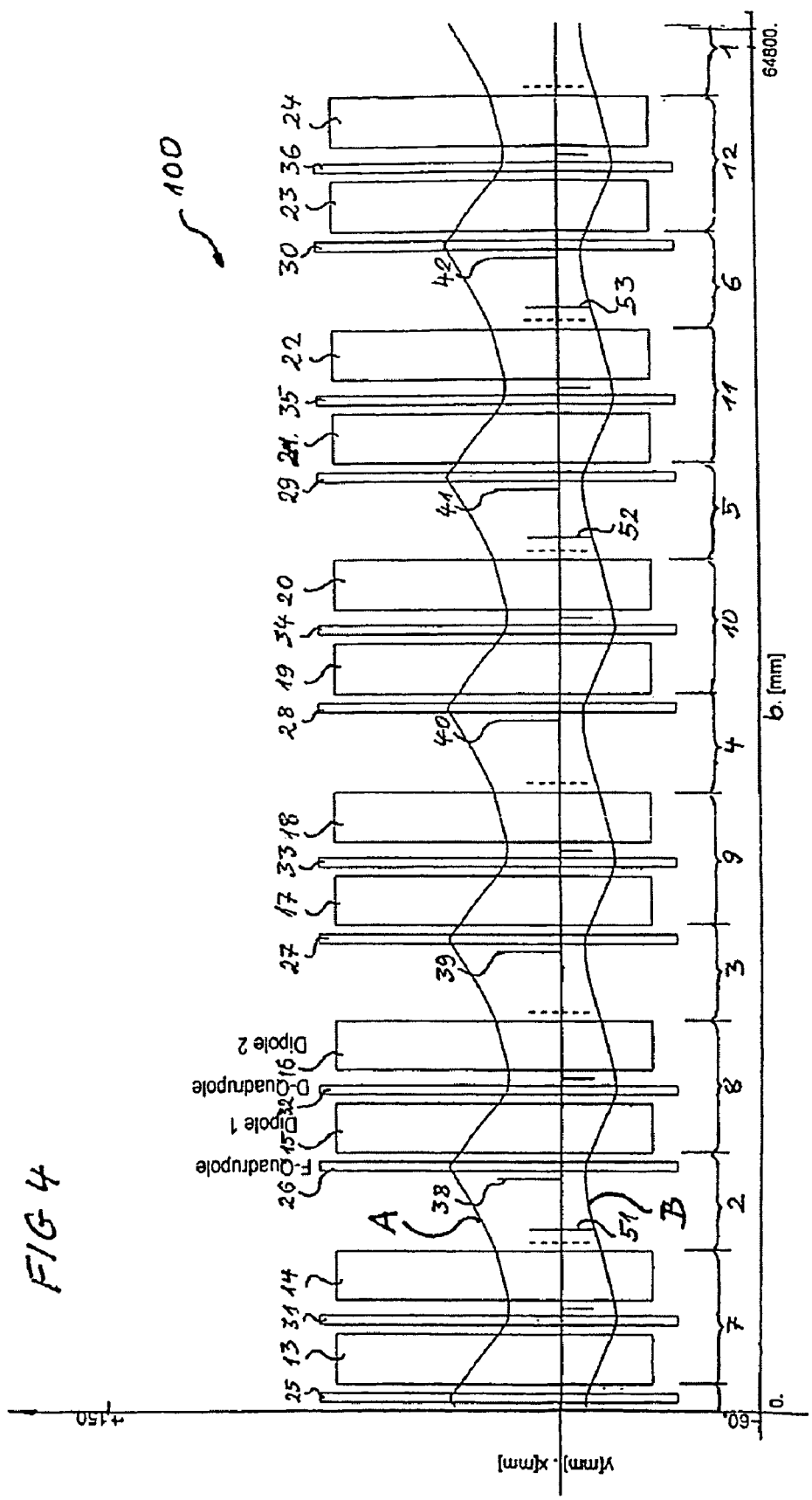
FIG. 4 shows schematically a diagram of the horizontal and vertical beam radii (beam envelopes) in the synchrotron ring according to FIG. 1.

FIG. 4 shows schematically a diagram with horizontal beam radii in the x-direction with curve A and with vertical beam radii in the y-direction with curve B, each of which are plotted in millimetres on the ordinate of the diagram. Components having the same functions as in the preceding Figures are marked with the same reference numerals and are not discussed separately. The trajectory length b in millimetres in the synchrotron ring is represented along the abscissa of the diagram. The beam deflections in the x and y directions in millimetres are, with comparable side constraints vis-à-vis known synchrotron rings, distinctly smaller, so that advantageously smaller aperture dimensions $a_x$ and $a_y$, as shown in FIG. 2, can be achieved with this invention.

Figure 5:
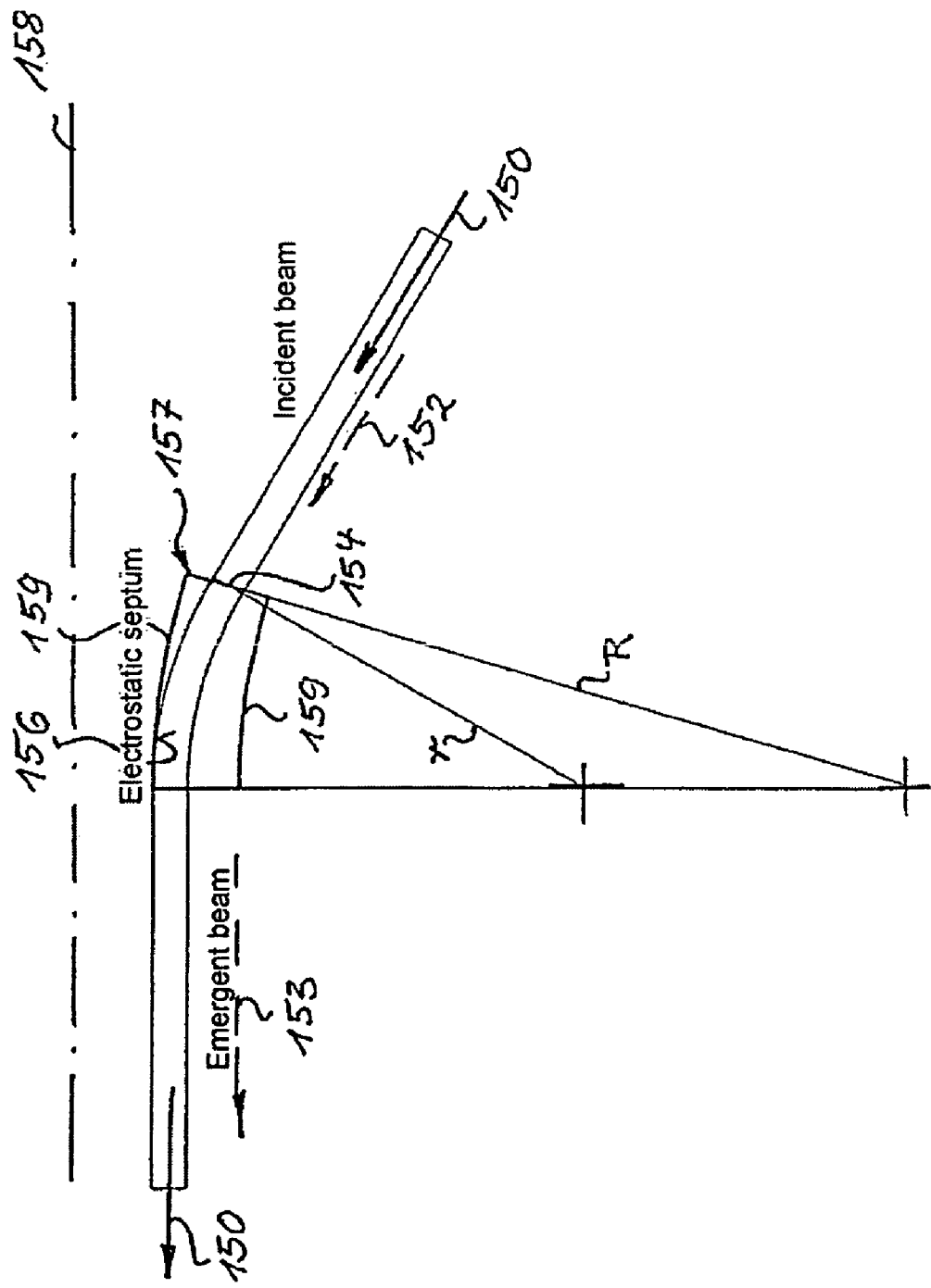
FIG. 5 shows a schematic plan view of an electrostatic injection septum.

FIG. 5 shows a schematic plan view of an electrostatic injection septum 157, which belongs to the injection system according to the invention for the synchrotron. The dot-dash line 158 indicates the position of the trajectory centre of a rectilinear beam section into which, by means of the injection means 43 shown in FIG. 1, an ion beam 150 is to be injected in the multi-turn injection method. The injection septum 157 according to the invention is designed so that a reproducible operation with minimum beam loss can be automatically set. For that purpose, the electrostatic injection septum 157 has an optimum geometry with beam entry 154 in the centre of the aperture of the electrostatic injection septum 157 for the incident ion beam 152 and beam exit 155 at the inner electrode 156 of the injection septum 157 for the outgoing ion beam 153, and a precise setting of beam position and beam angle at the beam exit 155 is achieved by adjusting two parameters, namely, deflection voltage at the electrostatic injection septum 157 and angle of incidence of the injected ion beam 150 at the beam entry 154 into the injection septum 157. For that purpose, the electrostatic injection septum 157 comprises curved electrostatic deflectors 159, the radii of curvature R of which are larger than the trajectory radius r of the pre-accelerated, injected and deflected ion beam 150.

Figure 6:
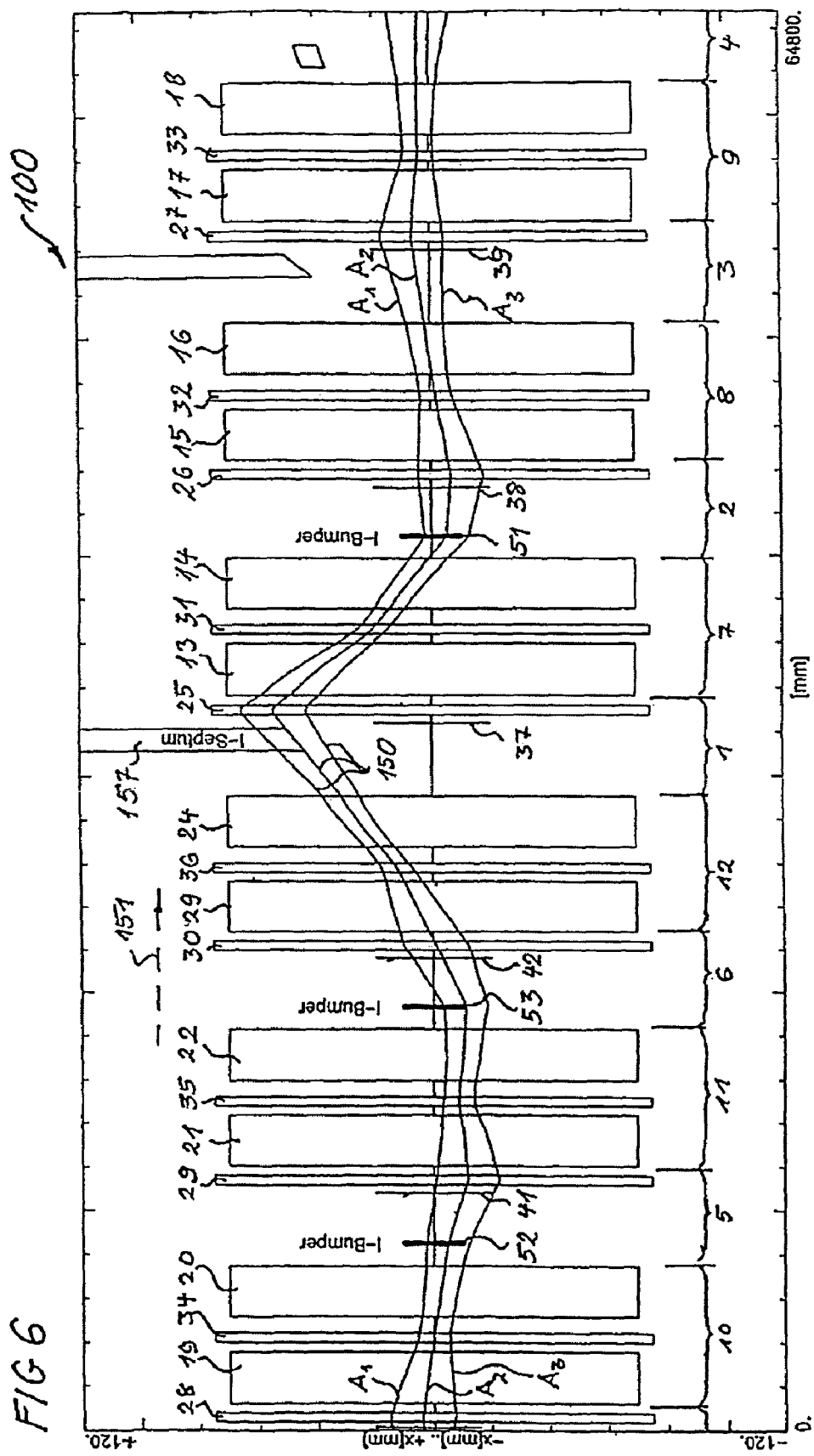
FIG. 6 shows schematically a diagram of the trajectory displacement of the ion beam in the synchrotron ring according to FIG. 1 under the influence of three bumper magnets in the beam path.

FIG. 6 shows schematically a diagram of the trajectory displacements of the ion beam 150 in the synchrotron ring 100 according to FIG. 1 under the influence of three bumper magnets 51, 52 and 53 in the beam path. This trajectory displacement with the beam envelope $A_1$, $A_3$ around the beam centre $A_2$ manages with three fast ferrite magnets to produce a local trajectory interruption outside the injection section 1 in the synchrotron, instead of the arrangement known in the art with one of the there bumper magnets in the injection section 1. In this example, two bumper magnets 52 and 53 in the straight sections 5 and 6 are inserted in the beam direction 151 before the injection section 1 with the injection septum 157, and one bumper magnet 51 is inserted after the rectilinear injection section 1, so that the injection section 1 tightly packed with the injection septum 157 shown in FIG. 5, the sextupole magnet 37 and the horizontally focusing quadrupole magnet 25, advantageously remains free of bumper magnets. In a further optimising step, optionally the two first bumper magnets 52 and 53 can be replaced by a single bumper magnet.

Figure 7B:
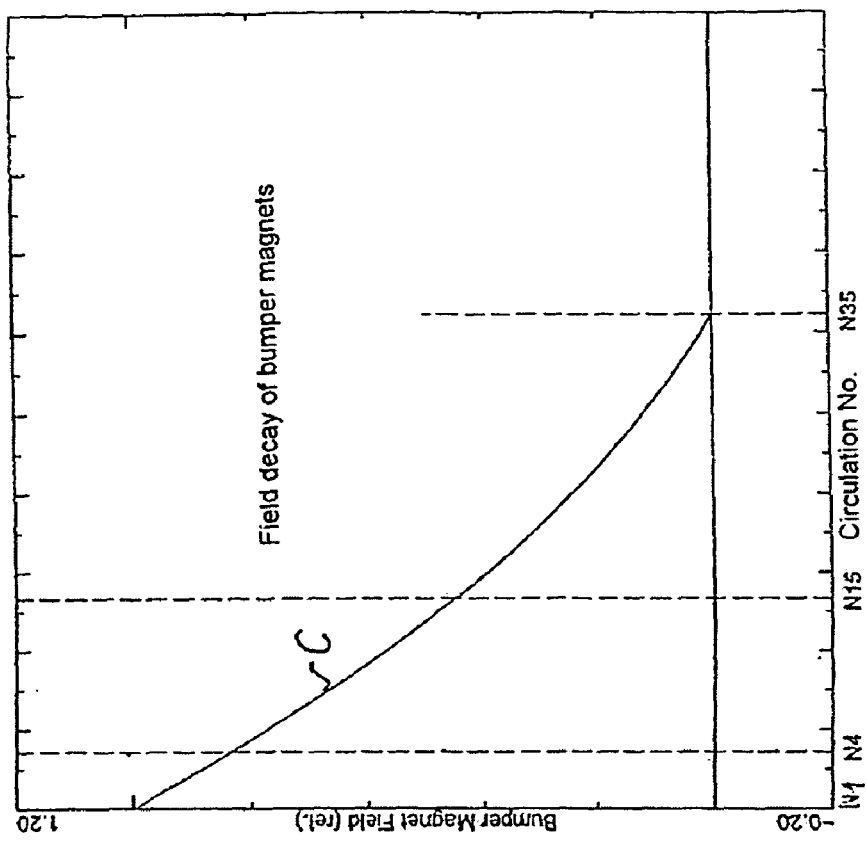
FIG. 7 shows schematically a diagram of a radial acceptance, triggered by bumper magnets, from circulation to circulation of the ion beam, and a parabolic ramp for the magnetic fields of the bumper magnets.
Figure 7A:
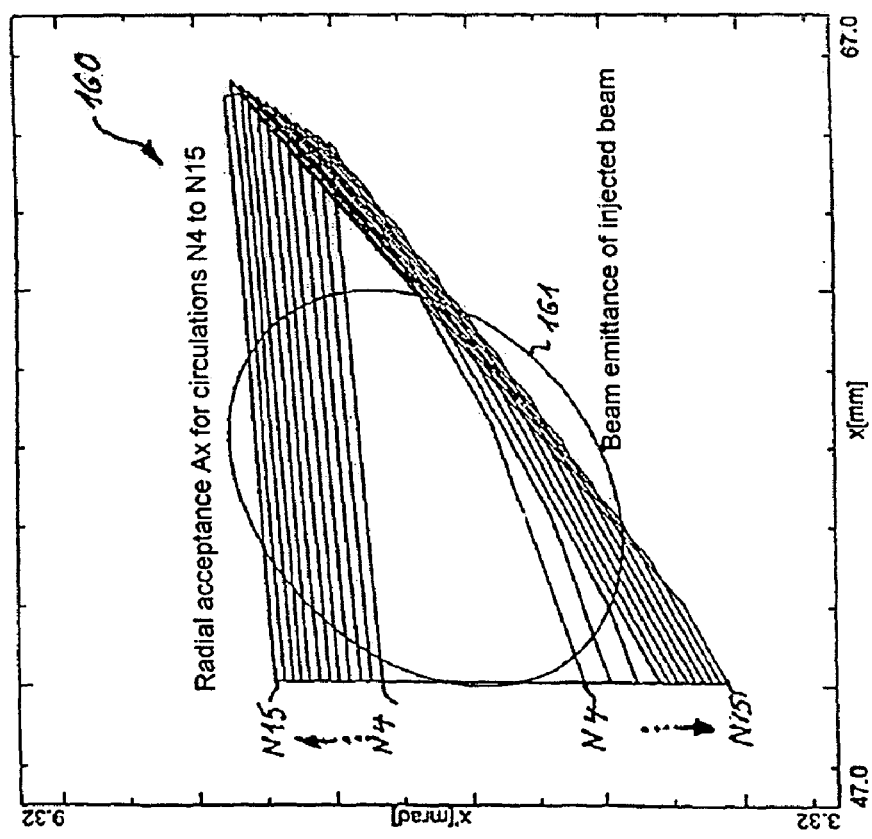

FIG. 7 shows schematically, in FIG. 7a, a diagram of the phase space 160 of a radial acceptance improving from circulation to circulation (N4 to N15) of the ion beam, the angle co-ordinates of the phase space 160 being shown in mrad on the ordinate and the location co-ordinates x being shown in mm on the abscissa. The ellipse 161 shows the achievable optimum adjustment of the beam emittance of the injected ion beam and the acceptance variable from circulation to circulation N4 to N15 for the multi-turn injection.

This radial acceptance is initiated by the three bumper magnets 51, 52 and 53, as shown in FIG. 6, by means of a parabolic ramp C, shown in FIG. 7b, for the magnetic fields of the bumper magnets. The diagram in 7b shows the relative intensity of the bumper magnetic field of the bumper magnets 51, 52 and 53 on the ordinate and the number of circulations N1 to N35 on the abscissa. The parabolic ramp C for the magnetic fields of the bumper magnets initially has a steep drop and a course that flattens out at the end of the ramp C.

The injection system described in FIGS. 5, 6 and 7 for the particle accelerator according to the invention has the following advantages:

(a) optimum construction at minimal cost,
(b) high efficiency for the multi-turn injection of about 85%, i.e. minimum beam loss during injection and correspondingly minimum radioactive burden, so that, unlike cyclotron accelerators, this synchrotron ring 100 according to the invention satisfies the requirements of radiation protection regulations,
(c) safe, reproducible adjustment methods, which are largely automated.

In addition, the injection means 43 according to the invention for what is termed multi-turn injection is improved as follows:

(a) non-linear, e.g. parabolic ramp C for the bumper magnetic fields with a steep drop at the start of the ramp C and a course that flattens out at the end of the ramp C;
(b) trajectory displacement by a multi-turn injection system having three optimally arranged so-called bumper magnets 51, 52 and 53, two of these magnets 52 and 53 in the two rectilinear sections 5 and 6 before the injection section 1 deflecting the ion beam 150 out and a third bumper magnet 51 in the rectilinear section 2 after the injection section 1 deflecting the ion beam 150 back in;
(c) instead of the known arrangement with three bumper magnets, wherein one is arranged in the injection section 1, only two or at most three bumper magnets are used, none of the bumper magnets 51, 52 and 53 being used in the very tightly packed rectilinear beam section 1 with injection means 43;
(d) optimum geometry for the electrostatic injection septum 157 with beam entry 154 in the centre of the aperture and beam exit 155 at the inner electrode 156 of the injection septum 157, and with a precise beam setting through adjustment of the two parameters deflection voltage at the electrostatic injection septum 157 and the angle of incidence, adjusted as far as possible automatically, of the injected ion beam 150 at the entry into the injection septum 157.

Figure 8:
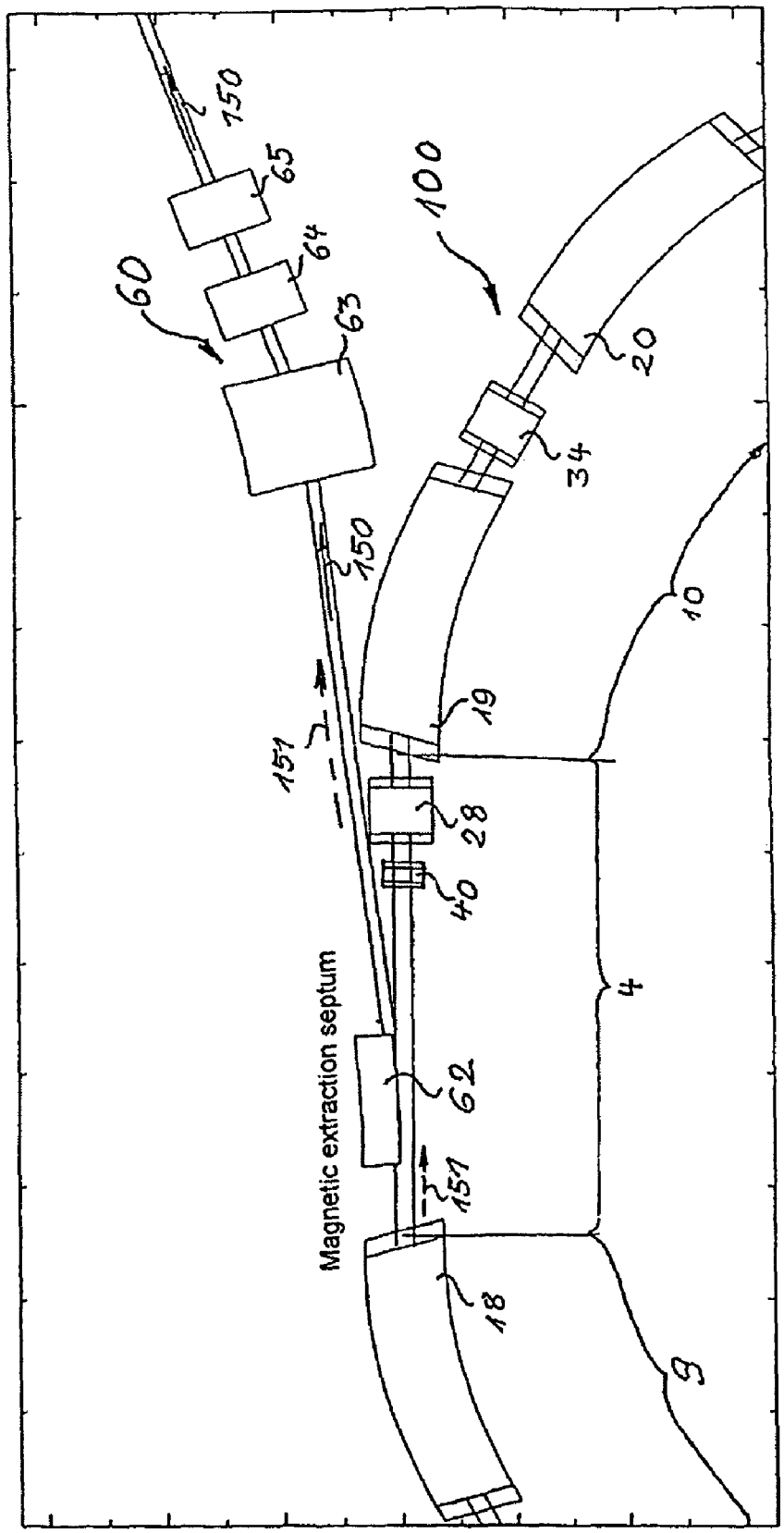
FIG. 8 shows schematically a plan view of a section of a sixfold synchrotron ring with the extraction branch.

FIG. 8 shows schematically a plan view of a section of a sixfold synchrotron ring 100 with the extraction branch 60, which branches off a rectilinear beam section 4 or extraction section 4. The beam deflection in the extraction section 4 comprises just one single extraction septum magnet 62, since the dimensions of the dipole magnet 19 of the dipole magnet pair 19/20 are reduced by virtue of the inventive synchrotron ring 100 such that the extraction of the ion beam 150 is effected at a shallower angle, unlike the situation in synchrotron rings known in the prior art, where at least two septum magnets are necessary in order, with a larger deflecting angle, to get past the subsequent larger dimensions of the dipole magnets used in the prior art.

The electromagnetic extraction septum 62 can be arranged so that it couples the extracted ion beam 150 into a horizontally deflecting dipole magnet 63, which delivers the ion beam

150 to two quadrupoles 64 and 65 arranged downstream on the extraction branch 60 and belonging to a high energy ion beam guidance system. In addition to the extraction septum magnet 62, the extraction system comprises an electrostatic extraction septum, which is arranged in the rectilinear beam section 3 upstream of the extraction section 4. Furthermore, for excitation of a non-linear resonance for the extraction, sextupoles 37 to 42 are arranged in each of the rectilinear beam sections 1 to 6.

FIG. 9 shows schematically a diagram of an individual emergent ray 71 of the extracted ion beam, the direction D of which can be adjusted in the phase space via excitation of a non-linear resonance achieved by the six sextupoles 37 to 42 shown in FIG. 1. For that purpose, FIG. 9 shows a representation of a phase space 170, the angle co-ordinate x' being shown on the ordinate of the diagram and the location co-ordinate x being visible on the abscissa of the illustration.

During the resonance extraction, the ions become unstable and, in the illustration, in the phase space 170 for the movement in the horizontal plane, move with each circulation one step from one of the three arms 71, 72, 73 to the next. Looking at the location co-ordinate x, they oscillate around the central desired trajectory 74 until in the last step on the linear lower arm 71 they enter the electrostatic extraction septum 61 shown in FIG. 11. Through the precise adjustment of the separatrix, the exit direction D for the extracted ion beam can be correspondingly adjusted by means of six individually adjustable sextupole magnets and the optimum efficiency for the resonance extraction can be set. In this way the complicated and laborious mechanical-geometrical adjustment of the electrostatic extraction septum 61 shown in FIG. 11 is avoided.

FIG. 10 shows schematically a diagram of a plurality of exit directions D to M of the extracted ion beam in the phase space 170, which are adjustable by means of the six individually adjustable sextupole magnets.

FIG. 11 shows schematically a diagram of the beam deflection in the synchrotron ring in the region of an extraction means 45. In the following FIGS. 12 to 15, components having identical functions to those in the preceding Figures are marked with the same reference numerals and are not separately discussed. The trajectory length b is again plotted in millimetres on the abscissa, but exclusively the deflection in the x-direction is plotted in millimetres on the ordinate. For extraction, by means of the six sextupole magnets, of which the sextupole magnets 39 and 40 of the synchrotron ring can be seen here, a non-linear extraction resonance is generated. An electrostatic extraction septum 61 is arranged upstream of an electromagnetic extraction septum 62 in the rectilinear beam section 3. The excitation of an extraction resonance has already been described above, the electrically and hence automatically adjustable sextupole magnets 37 to 42 enabling the exit direction D of the ion beam 150 to be precisely defined.

Figure 12:
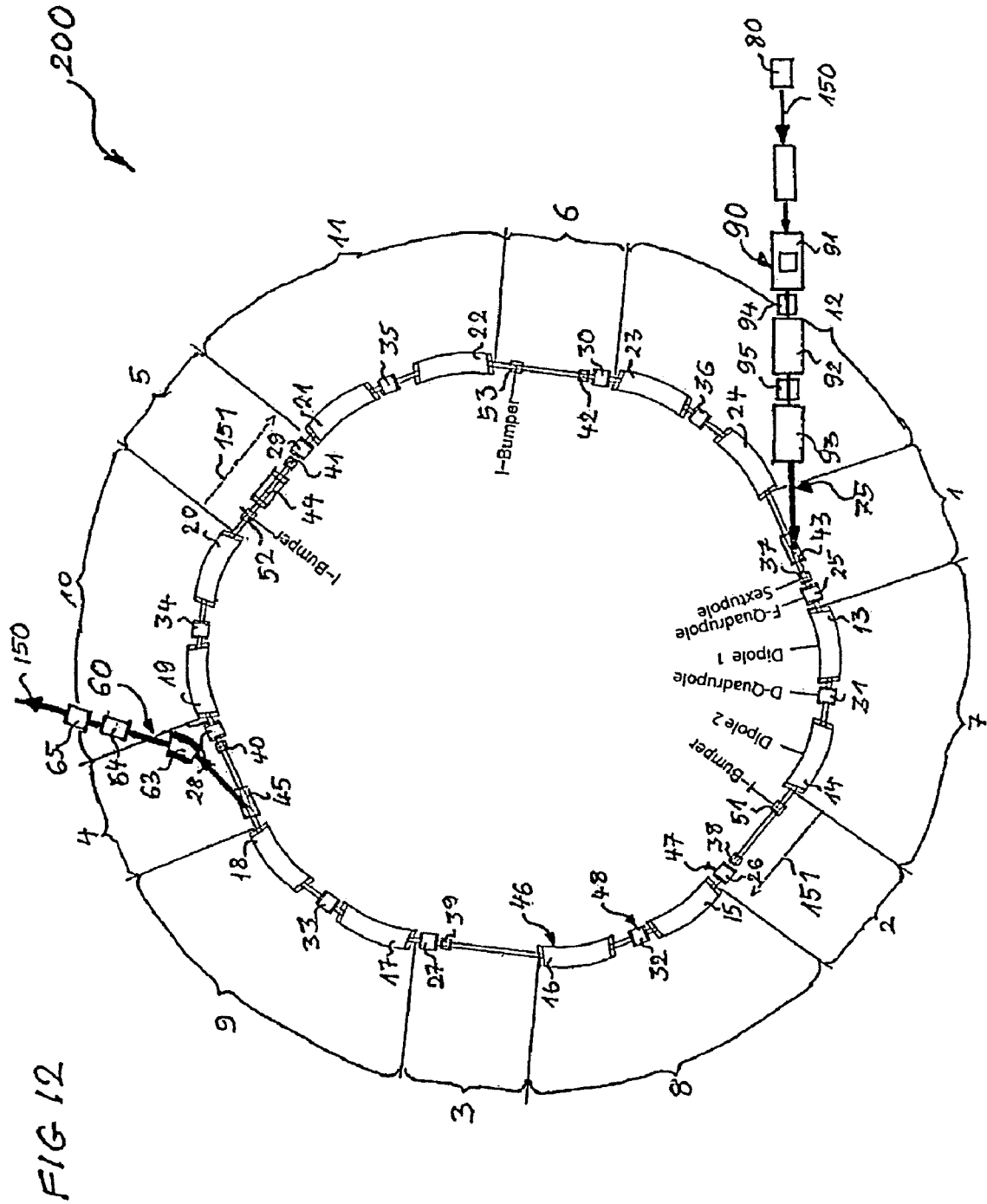
FIG. 12 shows schematically a plan view of a particle accelerator with ion source, injector-linear accelerator, sixfold synchrotron ring and extraction branch in one embodiment of the invention.

FIG. 12 shows schematically an overall view of a particle accelerator 200 with ion source 80, injector-linear accelerator 90, sixfold synchrotron ring 100, injection branch 75 and extraction branch 60 of one embodiment of the invention.

Figure 13:
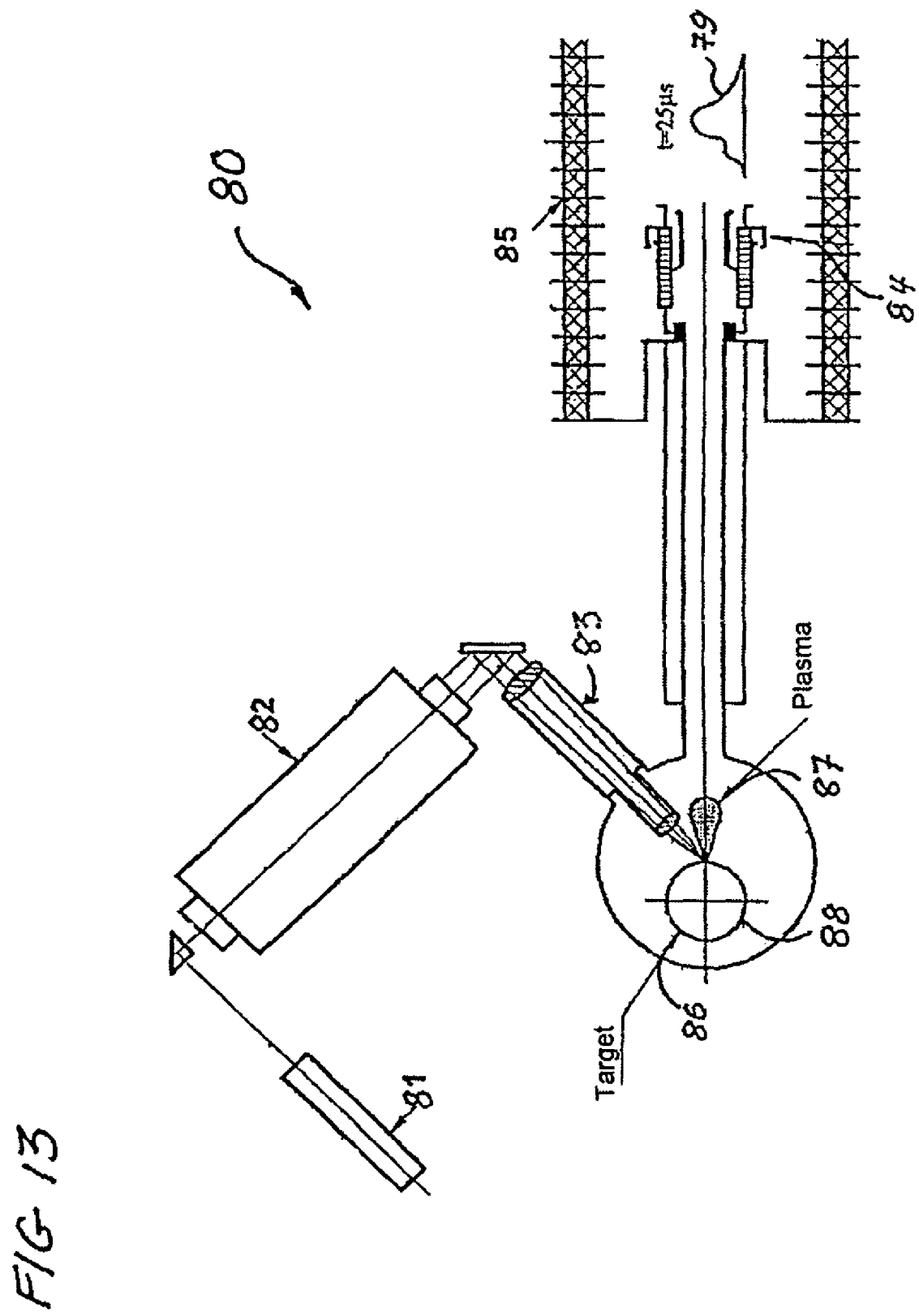
FIG. 13 shows schematically a basic outline of an ion source.

FIG. 13 shows schematically a basic outline of an ion source 80. The ion source used is a laser ion source, which comprises a HeNe laser 81, which for its part excites a $CO_2$ laser. The laser beam is then directed via an objective 83 onto the surface 88 of a carbon target or target 86, whereby the surface 88 of the carbon target is atomised to an electrically charged plasma 87. This plasma 87 is accelerated in a pre-accelerator 85.

This laser ion source 80 is especially suitable for generating very short beam pulses 79 of carbon ions less than or equal to 30 μs at high beam intensity. To generate ion beams, preferably carbon ions with the charge state q=4 ($C^{4+}$ ions), laser ion sources 80 offer important advantages over other ion sources:

(a) high beam intensities of more than $1 \times 10^{10}$ $C^{4+}$ ions in short beam pulses 79, preferably of from 20 μs to 30 μs duration;
(b) long operating life of many weeks without service;
(c) high reliability over many years of operation, and
(d) favourable investment and operating costs.

Figure 14:
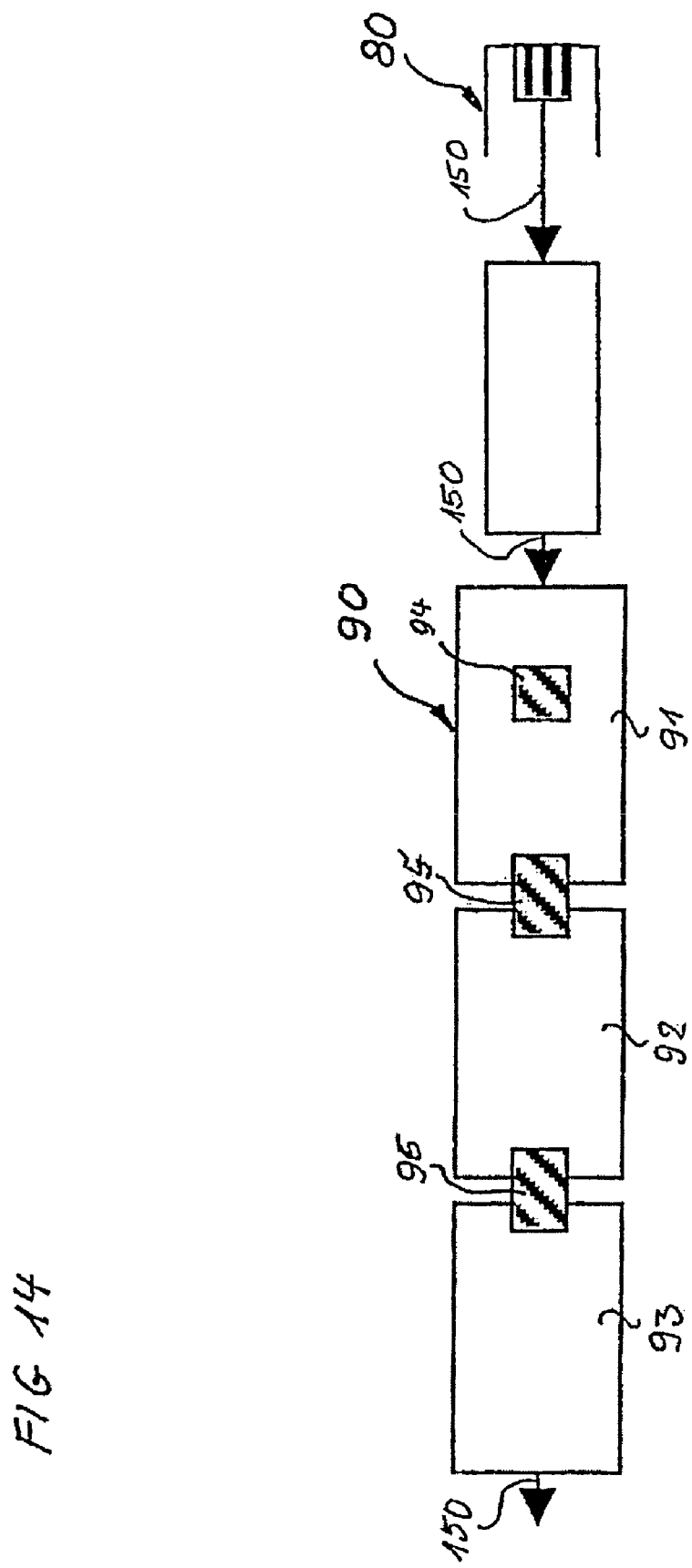
FIG. 14 shows schematically a basic outline of an injector-linear accelerator.

FIG. 14 shows schematically a basic outline of an injector-linear accelerator 90. The linear accelerator 90 is of modular construction with what are termed IH sections 91 to 93. In addition, three quadrupole triplets as quadrupole lenses 94 to 96 are arranged partially between the IH sections 91, 92 and 93. The modular construction of the high-frequency systems comprising IH sections 91 to 93 is achieved with high-frequency generators of at most 180 kW HF output. The arrangement of the quadrupole lenses 95 and 96 outside the vacuum system between the three accelerator sections in the form of the IH sections 91, 92 and 93, allows a simple, easy-to-service assembly of the linear accelerator.

This linear accelerator 90 of a preferred embodiment of the invention thus has the following advantages:

(a) modular construction of the linear accelerator 90 with three short accelerating sections of 1.5 m to 2 m long for each so-called IH section 91, 92 and 93,
(b) modular construction of the high-frequency systems with HF generators of at most 180 kW HF output with corresponding simplification compared with systems in the hitherto customary performance category 1 MW to 2 MW,
(c) technically simpler, and more advantageous for service, installation of the quadrupole lenses between the accelerator sections outside the vacuum system, at least for the quadrupole triplets 95 and 96.

Figure 15:
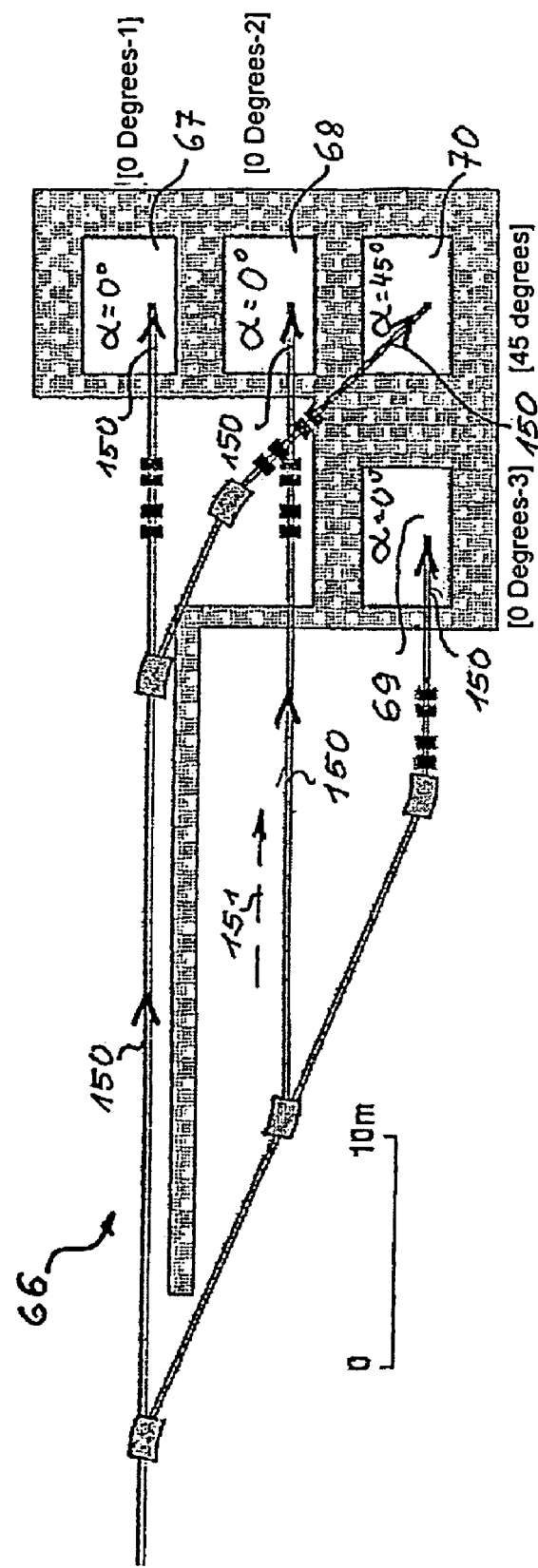
FIG. 15 shows schematically a lateral view of a beam guidance system for a plurality of irradiation sites.

FIG. 15 shows schematically a lateral view of a vertically deflected beam guidance system 66 to a plurality of radiotherapy rooms with irradiation sites 67 to 70. The beam guidance system 66 can operate between synchrotron and irradiation sites 67 to 70 with a horizontal deflection directly after the synchrotron, or have a separate vertical deflection for distribution of the ion beam 150 to the irradiation sites 67 to 70. For that purpose, for therapy the beam guidance system 66 between synchrotron and irradiation sites 67 to 70 is equipped either with a compensation of the horizontal dispersion directly after the synchrotron, or, for a distribution to the different irradiation sites 67 to 70, with a vertical deflection for a separate, independent compensation of the vertical dispersion. A high stability of the beam position at the irradiation sites 67 to 70 is therewith advantageously achieved. In FIG. 15, this arrangement is illustrated using the example of a beam guidance system 66 for four irradiation sites 67 to 70, the beam guidance system 66 being designed for three irradiation sites 67 to 69 with the angle of incidence α at 0° and one irradiation site 70 with the angle of incidence α at 45° from above.

To recapitulate, the invention relates to a particle accelerator for radiotherapy by means of ion beams, wherein by combining optimisations of all the important accelerator components, such as ion sources, injector linear accelerator, synchrotron ring and beam guidance systems, a reduction in investment costs and operating costs and an improvement in operational reliability are achieved. For that purpose, some or all mentioned improvements can be combined. A particle accelerator improved in this way has the following advantages:

(a) small magnet apertures with large beam acceptance;
(b) low magnet weights;
(c) small pulse powers and low energy consumption for operation of the synchrotron magnets; and
(d) optimised parameters for the design and for operation of the injection and extraction systems for the ion beam.

LIST OF REFERENCE NUMERALS 1-6 Rectilinear beam section
7-12 Curved beam section
13-24 Dipole magnets
13/14 Dipole pair
15/16 Dipole pair
17/18 Dipole pair
19/20 Dipole pair
21/22 Dipole pair
23/24 Dipole pair
25-30 Horizontally focusing quadrupole
31-36 Horizontally defocusing quadrupole
37-42 Sextupole
43 Injection means
44 Beam acceleration means
45 Extraction means
46 Bending magnet
47 Focusing magnet
48 Defocusing magnet
49 Magnet coil configuration
50 Laterally reversed half
51 Bumper
52 Bumper
53 Bumper
54 Elliptical profile
55 Pole piece configuration
56 Quadrant
60 Extraction branch
61 Electrostatic extraction septum
62 Electromagnetic extraction septum
63 Dipole magnet
64 Quadrupole magnet
65 Quadrupole magnet
66 Beam guidance system
67 Irradiation site
68 Irradiation site
69 Irradiation site
70 Irradiation site
71 Arm in phase space
72 Arm in phase space
73 Arm in phase space
74 Central beam trajectory
75 Injection path
79 Beam pulse
80 Ion source
81 HeNe laser
82 $CO_2$ laser
83 Objective
84 Ion-optical lens
85 Pre-accelerator
86 Target
87 Plasma
88 Surface of target
90 Linear accelerator
91 IH section
92 IH section
93 IH section
94 Quadrupole triplet
95 Quadrupole triplet
96 Quadrupole triplet
100 Sixfold synchrotron ring
150 Ion beam
151 Beam direction in synchrotron ring
152 Incident ion beam in an electrostatic extraction septum
153 Emergent beam from an injection septum
154 Beam entry
155 Beam exit
156 Inner electrode
157 Injection septum
158 dot-dash line
159 Deflector
160 Phase space
161 Ellipse
170 Phase pace
200 Particle accelerator
$\alpha$ Irradiation angle
$a_x$ Magnet aperture in horizontal direction
$a_y$ Magnet aperture in vertical direction
$A, A_1, A_2, A_3$ Trajectory course with horizontal deflection in x-direction
B Trajectory course with vertical deflection in y-direction
b Trajectory length in synchrotron
C Ramp
D-M Exit directions
N1-N35 Circulations of the ion beam
r Trajectory radius of the injected ion beam
R Radius of the electrostatic deflector
x' Angle co-ordinate
x Location co-ordinate

The invention claimed is:

1. A particle accelerator for radiotherapy with ion beams, comprising:
a synchrotron ring comprising rectilinear beam sections, curved beam sections, injector, extractor and at least one accelerator,
wherein at least one curved beam section comprises a pair of dipole magnets, and
a horizontally defocusing quadrupole magnet is arranged between the pair of dipole magnets, and horizontally focusing quadrupole magnet is provided upstream of the pair of dipole magnets in a rectilinear beam section directly preceding said respective curved beam section.

2. A particle accelerator of claim 1 wherein the particle accelerator comprises a sixfold synchrotron ring having six rectilinear beam sections and six curved beam sections, wherein, of the six rectilinear beam sections:
an injector for introducing a linearly accelerated ion beam into the synchrotron ring is arranged on a rectilinear beam section,
at least one accelerator for the ion beam is present along the course of another rectilinear beam section,
extractor for extracting the ion beam highly accelerated after several circulations is provided on a further rectilinear beam section,
the curved beam sections each comprise at least one dipole magnet, and wherein
each curved beam section comprises a pair of dipole magnets,
a horizontally defocusing quadrupole magnet is arranged between each pair of dipole magnets, and
a horizontally focusing quadrupole magnet is arranged upstream of each pair of dipole magnets in the rectilinear beam sections.

3. A particle accelerator of claim 1 wherein each pair of dipole magnets has a magnet coil configuration comprising a combination of a window-frame magnet type and an H-magnet type.

4. A particle accelerator of claim 1 wherein bumper magnets are arranged outside the rectilinear beam section for the injector in the other ones of the six rectilinear beam sections, in such a way that one bumper magnet is arranged downstream of the injector and at least one bumper magnet is arranged upstream of the injector.

5. A particle accelerator of claim 4 wherein for an injection of the ion beam within a limited number of circulations the bumper magnets have mains adapters and control units, which for control of a reducing exciter current provide a non-linear ramp having a flattened course at the end of the ramp.

6. A particle accelerator of claim 1 wherein the injector comprise an electrostatic injection septum, the curved electrostatic deflectors of which have a larger radius of curvature than the trajectory radius of the pre-accelerated, injected and deflected ion beam.

7. A particle accelerator of claim 1 wherein a sextupole magnet is provided upstream of each curved beam section with dipole magnet pair and quadrupoles.

8. A particle accelerator of claim 7 wherein the exciting currents of the individual sextupole magnets for a resonance extraction are adjustable, and the sextupole magnets are in operative connection with a fixed electrostatic extraction septum as one of the extractors for extracting the ion beam.

9. A particle accelerator of claim 1 wherein an extractor comprises a single extraction septum magnet as an electromagnetic extractor.

10. A particle accelerator of claim 1 wherein the particle accelerator comprises upstream of the sixfold synchrotron ring at least one ion source and an injector linear accelerator as particle accelerator components.

11. A particle accelerator of claim 1 wherein the particle accelerator comprises as ion source at least one laser ion source for the generation of beam pulses of carbon ions.

12. A particle accelerator of claim 10 wherein the particle accelerator comprises as injector linear accelerator a linear accelerator having IH section modules and, outside of vacuum systems between the IH section modules, quadrupole lens modules.

13. A particle accelerator of claim 1 wherein irradiation sites and sixfold synchrotron ring there is arranged a beam guidance system, which comprises a compensation of the horizontal dispersion directly after the synchrotron ring, or which, for the distribution by vertical deflection, provides a separate vertical compensation for the different irradiation sites.

14. A particle accelerator according to claim 13 wherein the beam guidance system for a plurality of irradiation sites can be supplied with different angles of incidence $\alpha$ with $0 \leq \alpha \leq 90°$, $0°$ being a horizontal angle of incidence $\alpha$ and $90°$ being an angle of incidence $\alpha$ impinging perpendicularly from above.

* * * * *